(12) United States Patent
Bootwala et al.

(10) Patent No.: US 10,729,554 B2
(45) Date of Patent: Aug. 4, 2020

(54) EXPANDABLE TRIALS

(71) Applicant: DePuy Synthes Products, Inc., Raynham, MA (US)

(72) Inventors: Zoher Bootwala, Foxboro, MA (US); Sean Saidha, Franklin, MA (US); William Frasier, New Bedford, MA (US); Thomas Martin, Riverside, RI (US); Shreedhar Kale, Barrington, RI (US); Laura Wilson, Basel (CH); Patrick Fatyol, Whitman, MA (US); John Olkowski, Boston, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 382 days.

(21) Appl. No.: 15/287,188

(22) Filed: Oct. 6, 2016

(65) Prior Publication Data
US 2017/0100256 A1 Apr. 13, 2017

Related U.S. Application Data

(60) Provisional application No. 62/329,589, filed on Apr. 29, 2016, provisional application No. 62/239,336, filed on Oct. 9, 2015.

(51) Int. Cl.
*A61F 2/44* (2006.01)
*A61F 2/30* (2006.01)

(52) U.S. Cl.
CPC ............ *A61F 2/4455* (2013.01); *A61F 2/442* (2013.01); *A61F 2002/30556* (2013.01); *A61F 2002/30579* (2013.01); *A61F 2002/30593* (2013.01); *A61F 2002/30621* (2013.01); *A61F 2002/30622* (2013.01); *A61F 2002/30934* (2013.01); *A61F 2220/0016* (2013.01)

(58) Field of Classification Search
CPC .................. A61F 2/442; A61F 2/4455; A61F 2002/4475; A61F 2002/30556; A61F 2002/30579; A61F 2002/30621–30622; A61F 2002/30934
USPC ........................................ 623/17.11–17.16
See application file for complete search history.

(56) References Cited

U.S. PATENT DOCUMENTS

| | | | |
|---|---|---|---|
| 7,488,330 B2 | 2/2009 | Stad | |
| 7,531,002 B2 | 5/2009 | Sutton | |
| 7,699,894 B2 | 4/2010 | O'Neil | |
| 7,862,618 B2 | 1/2011 | White | |
| 7,879,104 B2 * | 2/2011 | Dewey | A61B 17/7065 623/17.16 |
| 7,959,677 B2 | 6/2011 | Landry | |
| 8,172,903 B2 | 5/2012 | Gordon | |
| 8,182,538 B2 | 5/2012 | O'Neil | |
| 8,574,300 B2 | 11/2013 | McManus | |
| 8,679,183 B2 | 3/2014 | Glerum | |
| 8,845,733 B2 | 9/2014 | O'Neil | |

(Continued)

*Primary Examiner* — Jessica Weiss

(57) ABSTRACT

An expandable implant is made via a central strut having a pivotable arm on each end. The implant can be inserted into a disc space either horizontally or vertically with the arms in a closed position and then (if inserted horizontally) optionally rotated up into place. The arms are then pivoted out, thereby increasing the foot print of a horizontally inserted implant. The expanded implant can be locked in place through the use of an additional insert or ratchet that fits between the arms and locks the arms in place.

6 Claims, 15 Drawing Sheets

(56) References Cited

U.S. PATENT DOCUMENTS

| | | |
|---|---|---|
| 8,900,307 B2 | 12/2014 | Hawkins |
| 9,408,710 B2* | 8/2016 | Purcell .................... A61F 2/442 |
| 9,522,068 B2* | 12/2016 | Goel ..................... A61F 2/4455 |
| 9,615,935 B2* | 4/2017 | Patterson .............. A61F 2/4455 |
| 2005/0256576 A1* | 11/2005 | Moskowitz ............. A61F 2/441 |
| | | 623/17.12 |
| 2006/0069436 A1 | 3/2006 | Sutton |
| 2007/0149978 A1* | 6/2007 | Shezifi ................ A61B 17/025 |
| | | 606/90 |
| 2007/0276337 A1* | 11/2007 | Trieu ..................... A61B 17/58 |
| | | 604/181 |
| 2008/0114456 A1* | 5/2008 | Dewey ............... A61B 17/7065 |
| | | 623/17.16 |
| 2008/0125864 A1 | 5/2008 | de Villiers |
| 2009/0216330 A1 | 8/2009 | Geisert |
| 2009/0259316 A1* | 10/2009 | Ginn ................. A61B 17/7062 |
| | | 623/17.16 |
| 2010/0137987 A1* | 6/2010 | Diao ................. A61B 17/7095 |
| | | 623/17.15 |
| 2010/0280620 A1 | 11/2010 | Reichen |
| 2010/0298941 A1 | 11/2010 | Hes |
| 2011/0066192 A1* | 3/2011 | Frasier .................... A61F 2/441 |
| | | 606/86 A |
| 2011/0319999 A1* | 12/2011 | O'Neil ............... A61B 17/1671 |
| | | 623/17.16 |
| 2012/0004732 A1* | 1/2012 | Goel .................... A61F 2/4455 |
| | | 623/17.16 |
| 2012/0136448 A1* | 5/2012 | Seifert ............... A61B 17/1617 |
| | | 623/17.16 |
| 2012/0232660 A1 | 9/2012 | Davenport |
| 2013/0041471 A1* | 2/2013 | Siegal .................... A61F 2/442 |
| | | 623/17.16 |
| 2013/0116791 A1 | 5/2013 | Theofilos |
| 2013/0144388 A1* | 6/2013 | Emery ................ A61B 17/025 |
| | | 623/17.16 |
| 2013/0166027 A1 | 6/2013 | Bellas |
| 2014/0114420 A1 | 4/2014 | Robinson |
| 2014/0277490 A1 | 9/2014 | Perloff |
| 2015/0257894 A1* | 9/2015 | Levy ..................... A61F 2/442 |
| | | 623/17.15 |
| 2015/0282797 A1 | 10/2015 | O'Neil |
| 2015/0305878 A1 | 10/2015 | O'Neil |

\* cited by examiner

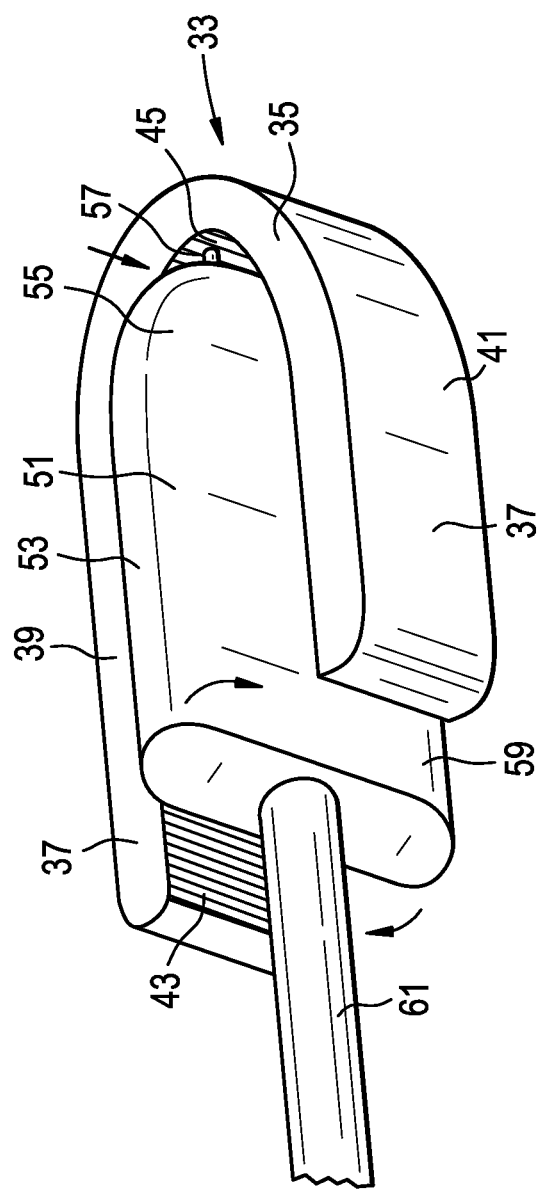

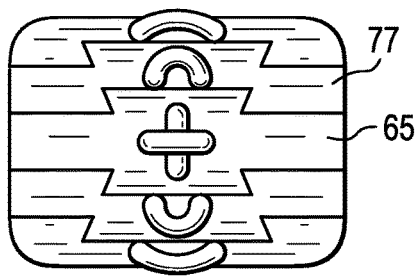
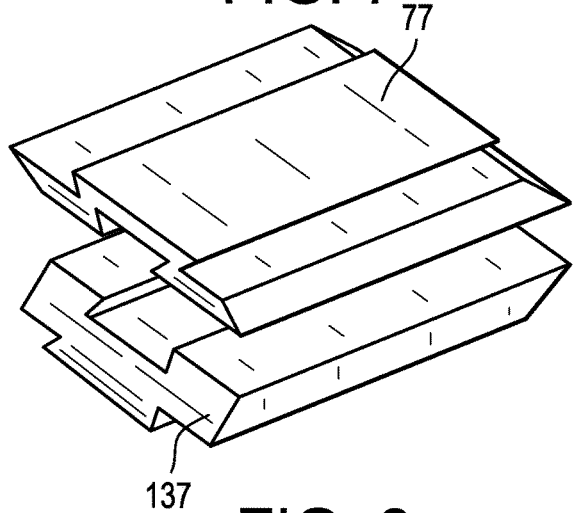
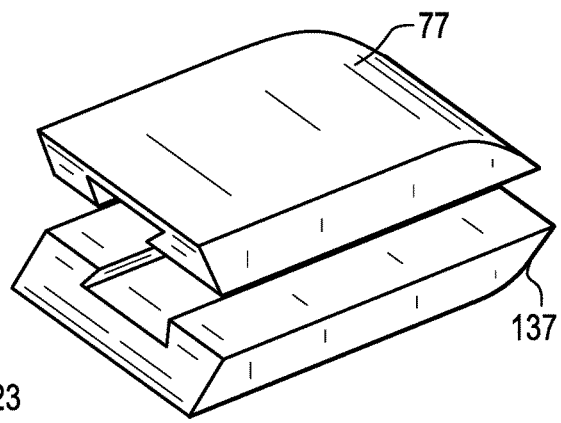
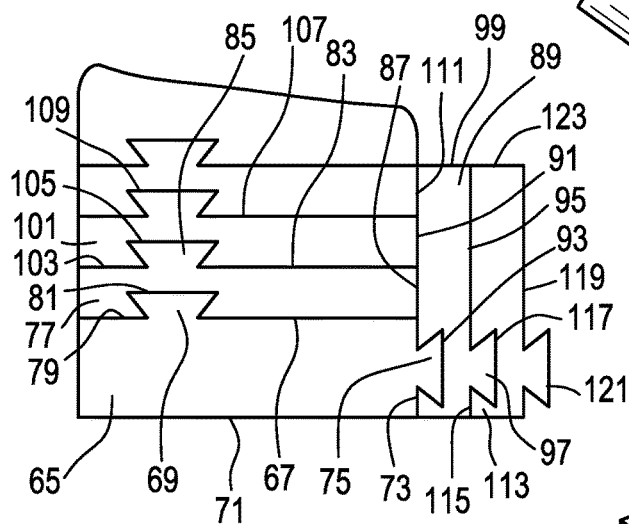
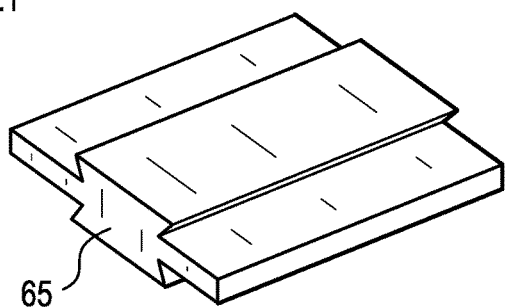

EXPANDABLE TRIALS

CONTINUING DATA

This patent application claims priority from US provisional application U.S. Ser. No. 62/329,589, filed Apr. 29, 2016 entitled "Expandable Trials" (Bootwala et al.), and from US provisional application U.S. Ser. No. 62/239,336, filed Oct. 9, 2015 entitled "Expandable Trials" (Bootwala et al.), the specifications of which are incorporated by reference in their entireties.

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint. One proposed method of managing these problems is to remove the problematic disc and replace it with a prosthetic disc that allows for the natural motion between the adjacent vertebrae ("a motion disc").

Prior to inserting the disc, however, the surgeon typically desires to insure that the properly sized implant has been identified for the particular patient. To this end, trial implants are commonly included within the instrument sets that allow the surgeon to temporarily insert the trial into the intervertebral disc space and assess whether the height and footprint of the trial would be appropriate for the actual implant to be inserted. Typically, a large number of trials are supplied in an instrument set, with each having a distinct height, lordotic angle and footprint.

More recently, fusion cages have been redesigned to provide a small profile during insertion into the disc space and then to expand to distract the disc space. The small profile of the initial configuration allows the surgeon to operate through a smaller opening, thereby minimizing surgical trauma. With the advent of these expandable cages, there is now also a need for an expandable trial as well.

SUMMARY OF THE INVENTION

In one embodiment, an expandable implant is made via a central strut having a pivotable arm on each end. The implant can be inserted into a disc space either horizontally or vertically with the arms in a closed position and then (if inserted horizontally) optionally rotated up into place. The arms are then pivoted out, thereby increasing the foot print of a horizontally inserted implant. The expanded implant can be locked in place through the use of an additional insert or ratchet that fits between the arms and locks the arms in place.

DESCRIPTION OF THE DRAWINGS

FIG. 5 discloses a spreader-based expandable device.
FIGS. 6-14 disclose expandable devices based upon stackable blocks.

DETAILED DESCRIPTION OF THE INVENTION

Figure 1:
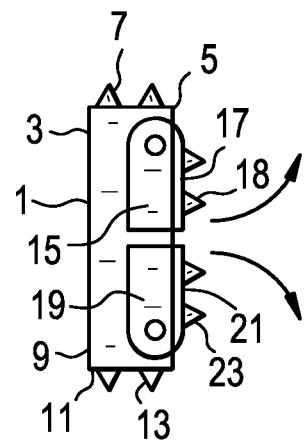
FIGS. 1-4 disclose a multi-plate expandable device.
Figure 2:
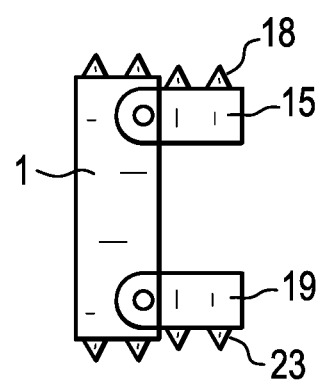
Figure 3:
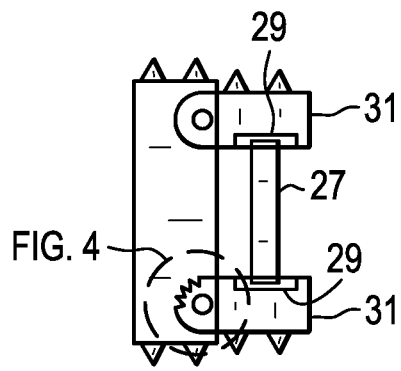
Figure 4:
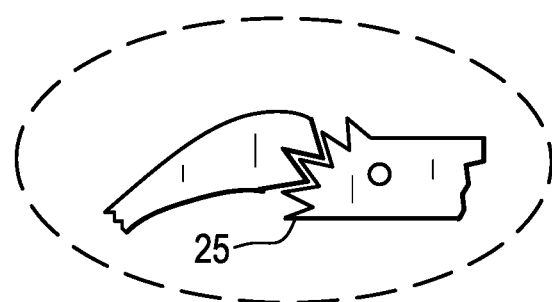

In accordance with FIGS. 1-4, there is provided an intervertebral device, comprising:
a) a first strut 1 comprising i) an upper portion 3 forming an upper surface 5 having teeth 7 adapted for gripping an upper natural endplate and ii) a lower portion 9 forming a lower surface 11 comprising teeth 13 adapted for gripping a lower natural endplate,
b) an upper arm 15 pivotally connected to the upper portion of the first strut and having an upper surface 17 having teeth 18 adapted for gripping an upper natural endplate, and
c) a lower arm 19 pivotally connected to the lower portion of the first strut and having a lower surface 21 having teeth 23 adapted for gripping a lower natural endplate,
wherein the upper surface of the first strut and the upper surface of the upper arm are substantially co-planar in an expanded condition,
wherein the lower surface of the first strut and the lower surface of the lower arm are substantially co-planar in an expanded condition.
Preferably, the pivotal connections between first strut and each arm each form a ratchet connection 25 adapted to lock the device in the expanded condition.
In some embodiments, the device further comprises:
d) a second strut 27 extending between a lower surface of the upper arm and an upper surface of the lower arm to lock the device in the expanded condition.
Preferably, each of the lower surface of the upper arm and the upper surface of the lower arm comprises a recess 29 adapted for reception of a respective end of the second strut.
Preferably, each arm has a first endface 31 opposite its pivotal connection, and the first endfaces are substantially opposed in an unexpanded condition.

Also in accordance with FIGS. 1-4, there is provided: a method of using an intervertebral device, comprising the steps of:
a) inserting the intervertebral device of claim 1 into a disc space in its unexpanded condition,
b) moving each arm so that the device adopts its expanded condition,
c) locking the device in its expanded condition.

Footprint/Spreader

In a FIG. 5 embodiment, there is provided a spreader trial in which a U-shaped element houses a spreader having a substantially rectangular axial cross-section, wherein the height of the cross-section is less than its width. The spreader is rotatably coupled to the apex of the U-shaped element. These two elements are inserted into the disc space as one piece, with a rotatable shaft carrying the spreader and coupled to the apex of the U-shaped element. The U-shaped element is inserted so that each leg of the U-shaped is substantially parallel to the adjacent vertebral endplates (i.e., the U-shaped spreader cross-section provides a minimum height), while the spreader is inserted so that its height is extending between the endplates and a minimum height is established. Once inserted, the shaft is rotated about 90 degrees so that the spreader width is now extending between the endplates so that the spreader displays its maximum height. This condition preferably produces distraction of the disc space. Bone filler can then be added around the spreader within the U-shaped element.

In accordance with FIG. 5, there is provided an intervertebral device comprising:
  a) a substantially U-shaped element 33 comprising a substantially C-shaped portion 35 and a pair of arms 37 extending therefrom, an upper surface 39 adapted for gripping a natural endplate, a lower surface 41 adapted for gripping a natural endplate, and an inner surface 43 including a concave surface 45, the concave surface having a first threaded coupling extending therein, wherein the inner surface defines a cavity, wherein a first distance between the upper and lower surfaces defines a first height, and wherein a second distance between the inner surfaces of the arms defines a width of the cavity,
  b) a spreader element 51 having i) a block 53 having a first end 55 having a second threaded coupling 57 that mates with the first threaded coupling, a second end 59, a second height and a width, wherein the height is less than the width, ii) a shaft 61 extending from the second end of the block and iii) a handle (not shown) connected to the shaft,
wherein the first and second threaded couplings threadably mate,
wherein the width of the block is less than the width of the cavity so that the block of the spreader element is received in the cavity of the U-shaped element.

Also in accordance with FIG. 5, there is provided a method of preparing a disc space between opposed vertebral endplates, comprising the steps of:
a) inserting the intervertebral device of FIG. 5 into a disc space wherein the block is oriented so that the height of the block spans the opposed vertebral endplates
b) rotating the block by about 90 degrees so that the width of the block spans the opposed vertebral endplates, thereby distracting the disc space.
  Preferably, this method further comprises the steps of:
    c) disengaging the spreader from the U-shaped element, and
    d) removing the block from the disc space.
  Also preferably, this method further comprises the steps of:
    e) contacting the U-shaped element with an implant material.

Stackable Blocks

In a FIGS. 6-9 embodiment, a plurality of stackable spacers are inserted in sequence to build an implant of a desired height and preferably width. Preferably, the spacers are designed so that the subsequent spacers can be added both in the vertical and lateral directions. Preferably, endcap spaced are also utilized that cap off the vertical dimension and provide lordosis. In one embodiments, the endcaps have vertical throughholes and legs extending towards each other that are designed to mate, so that once the endcaps are placed and mated, the intermediate spacers can be removed and a hollow fusion cage results.

In accordance with FIGS. 6-9, there is provided an intervertebral device comprising:
  a) a base block 65 having an upper surface 67 having a first mating feature 69, a lower surface 71 and a first side surface 73 having a second mating feature 75 therebetween,
  b) a first upper spacer 77 having a lower surface 79 having a third mating feature 81, and an upper surface 83 having a fourth mating feature 85, and a side surface 87 therebetween
  c) a first lateral spacer 89 having an inner side surface 91 having a fifth mating feature 93, an outer side surface 95 having a sixth mating surface 97 therebetween, and an upper surface 99 therebetween,
wherein the first mating feature of the base block slidably mates with the third mating feature of the first upper spacer, and
wherein the second mating feature of the base block slidably mates with the fifth mating feature of the first lateral spacer.

In some embodiments, each mating feature is a dovetail feature.

Preferably, the device further comprises:
  d) a second upper spacer 101 having a lower surface 103 having a seventh mating feature 105, and an upper surface 107 having a eighth mating feature 109, and a side surface 111 therebetween
  e) a second lateral spacer 113 having an inner side surface 115 having a ninth mating feature 117, an outer side surface 119 having a tenth mating surface 121 therebetween, and an upper surface 123 therebetween,
wherein the fourth mating feature of the first upper spacer slidably mates with the seventh mating feature of the second upper spacer, and
wherein the sixth mating feature of the first lateral spacer slidably mates with the ninth mating feature of the second lateral spacer.

Preferably, the device further comprises:
  f) a third upper spacer having a lower surface having an eleventh mating feature, an upper surface disposed at an angle to its lower surface, and a side surface therebetween,
  wherein the third upper spacer is disposed above the second vertical spacer.

Preferably, the eleventh mating feature of the third vertical spacer is located substantially directly above the eighth mating surface of the second vertical spacer.

FIG. 10 discloses a central insert 65 within the stackable blocks.

Figure 11:
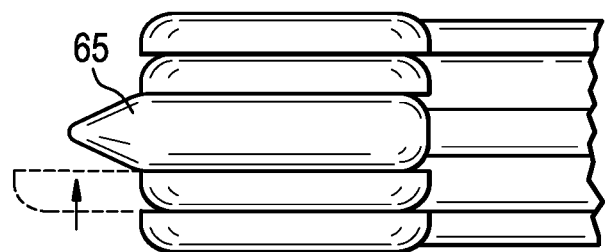
Figure 12:
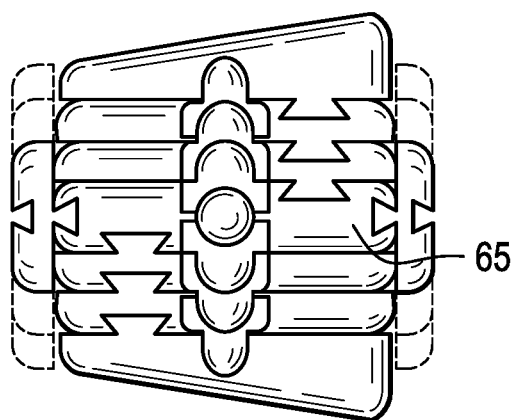

Also in accordance with FIGS. 11-12, there is provided other stackable designs with various inserts 65.

Figure 13A:
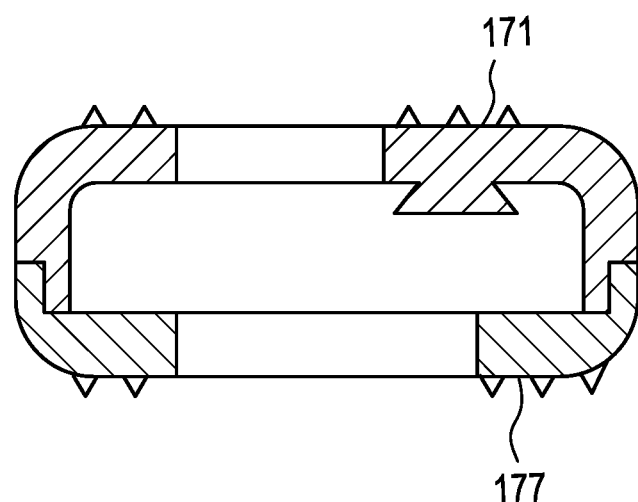
Figure 13B:
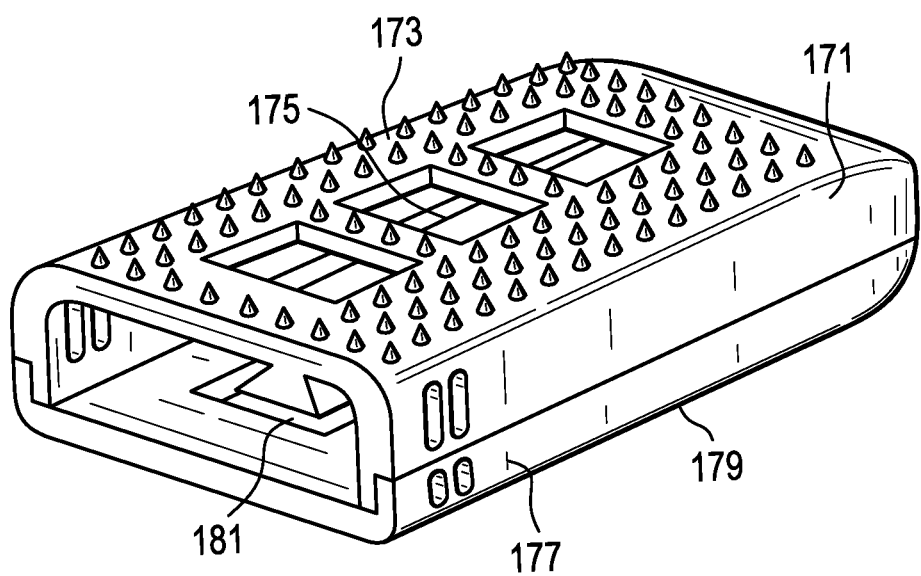
Figure 14:
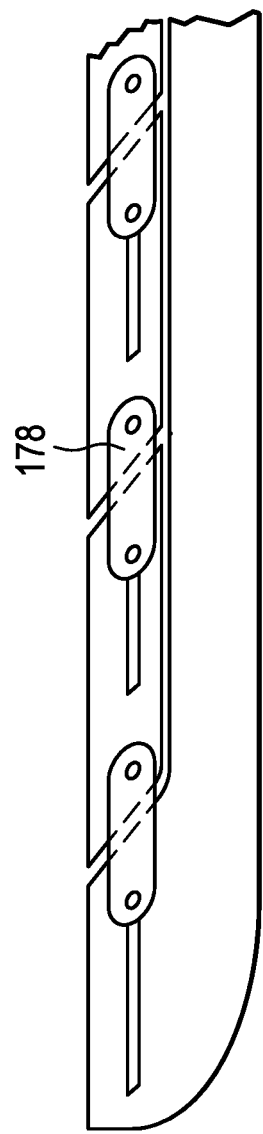

In a FIG. 13a-14 embodiment, there is an intervertebral device comprising:
  a) an upper shell 171 having an upper surface 173 having a throughhole 175 therethrough and opposed sidewalls,
  b) a lower shell 177 having a lower surface 179 having a throughhole 181 therethrough and opposed sidewalls,
  c) a plurality of stacked spacers disposed between the upper shell and the lower shell, wherein each spacer shares with its adjacent spacer a mating interface comprising a pair of mating features,
  wherein the opposed sidewalls of the upper shell mate with the opposed sidewalls of the lower shell.

In some embodiments, there is a method of building a fusion cage comprising:
  inserting into a disc space a plurality of stacked spacers, wherein each spacer shares with its adjacent spacer a mating interface comprising a pair of mating features, the plurality having an uppermost spacer having an upper mating feature and a lowermost spacer having a lower mating feature,
  attaching to the uppermost spacer an upper shell having an upper surface having a throughhole therethrough, a lower surface having a lower mating feature and opposed sidewalls, wherein the upper mating feature of the uppermost spacer mates with the lower mating feature of the upper shell, attaching to the lowermost spacer a lower shell having an lower surface having a throughhole therethrough, an upper surface having an upper mating feature and opposed sidewalls, wherein the lower mating feature of the lowermost spacer mates with the upper mating feature of the lower shell, attaching the sidewalls of the upper shell to the sidewalls of the lower shell, removing the plurality of stacked spacers from the disc space to create a void between the upper and lower shells, and filling the void with a bone filler.

FIG. 14 discloses trial heights sections with the links section 178. As the clinician pushes the trial sections forward, they will ride up the ramps of each other with the aid of link sections holding them all together. As the trail sections are stacked, this will determine the disc height for the appropriate implant.

Spring

Figure 15:
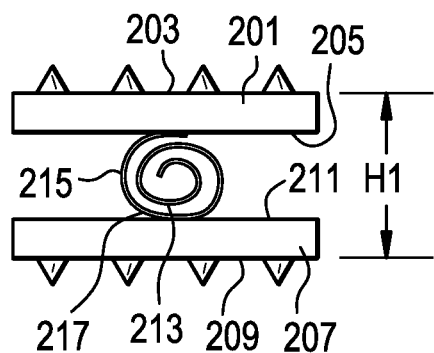
FIGS. 15-20 disclose spring-based expandable designs.

In the FIG. 15 embodiment, a torsion spring is provided between implant endplates in a collapsed configuration having a height H1. Once the tension in the spring is released, the spring expands, thereby increasing the height between the endplates to an expanded height H2. The torsion spring could also be made from one or more nitinol leaf springs that expand through temperature change or mechanical means. Once the implant is expanded, the spaced between the endplates can be filled with bone graft or a monolithic insert.

In accordance with FIG. 15, there is provided:

an intervertebral device comprising;
a) a first endplate 201 having an outer surface 203 adapted for gripping a first natural endplate and an inner surface 205,
b) a second endplate 207 having an outer surface 209 adapted for gripping a second opposed natural endplate and an inner surface 211,
c) a torsion spring 213 having a first portion 215 contacting the inner surface of the first endplate and a second portion 217 contacting the inner surface of the second endplate, the device having an unexpanded state and an expanded state, wherein the torsion spring is tensioned in the unexpanded state and released in the expanded state.

Figure 16:
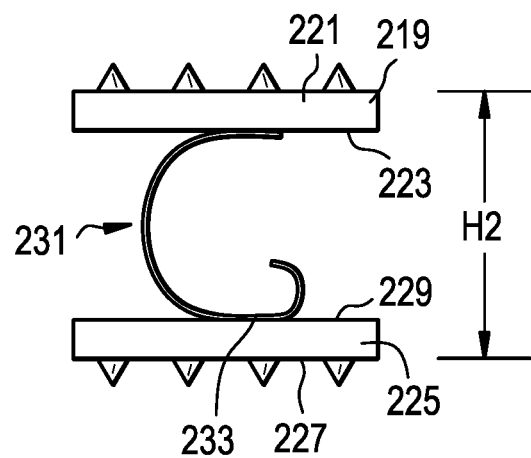

Also in accordance with FIG. 16, there is provided an intervertebral device comprising;
a) a first endplate 219 having an outer surface 221 adapted for gripping a first natural endplate and an inner surface 223,
b) a second endplate 225 having an outer surface 227 adapted for gripping a second opposed natural endplate and an inner surface 229,
c) a memory metal leaf spring 231 having end portions contacting the inner surface of the first endplate and an intermediate portion 233 contacting the inner surface of the second endplate, the device having an unexpanded state and an expanded state, wherein the leaf spring is under force in the unexpanded state and released in the expanded state.

Figure 17:
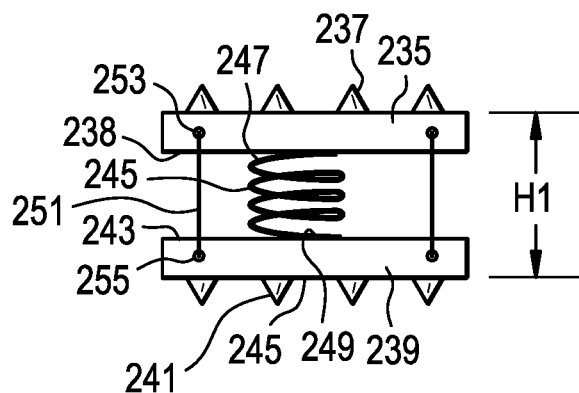
Figure 18:
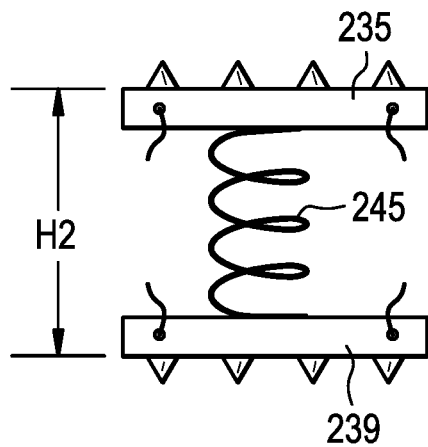

In a FIG. 17-18 embodiment, tethers are used to hold a coil spring in a collapsed state so that an implant has a collapsed height H1. The tethers can be cut or removed after insertion, thereby allowing the implant to expand under spring tension to a height H2. The space between the endplates can be filled with bone graft or a monolithic insert. The tension of the spring can be adjusted by using different springs.

In one embodiment, three springs increasing force are provided sequentially between endplates. The release of the varying tensions in the springs produces lordosis. Additionally, the expanded endplates can be held open in all of these spring embodiments through a mechanical means such as a cam locking mechanism.

In accordance with FIGS. 17-18, there is provided an intervertebral device comprising;
a) an upper endplate 235 having an upper surface 237 adapted for gripping an upper natural endplate and a lower surface 238,
b) a lower endplate 239 having a lower surface 241 adapted for gripping a lower natural endplate and an upper surface 243,
c) a coil spring 245 having a first endportion 247 contacting the lower surface of the upper endplate and a second endportion 249 contacting the upper surface of the lower endplate,
d) a tether 251 having a first endportion 253 contacting the lower surface of the upper endplate and a second endportion 255 contacting the upper surface of the lower endplate, the device having an unexpanded state and an expanded state, wherein the coil spring is tensioned in the unexpanded state and released in the expanded state, wherein the tether is tensioned in the unexpanded state and severed in the expanded state.

Figure 19:
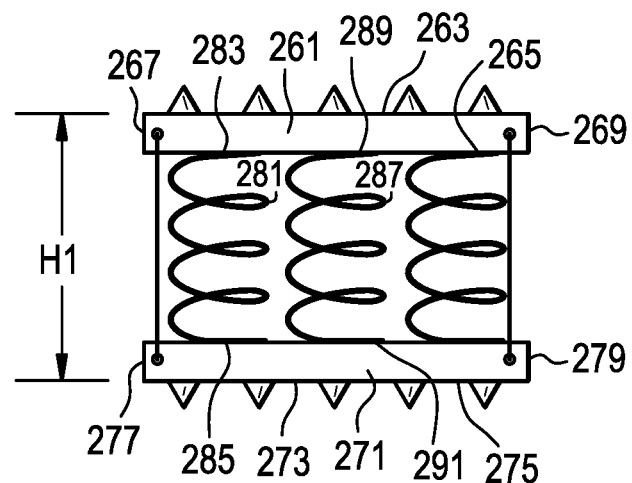
Figure 20:
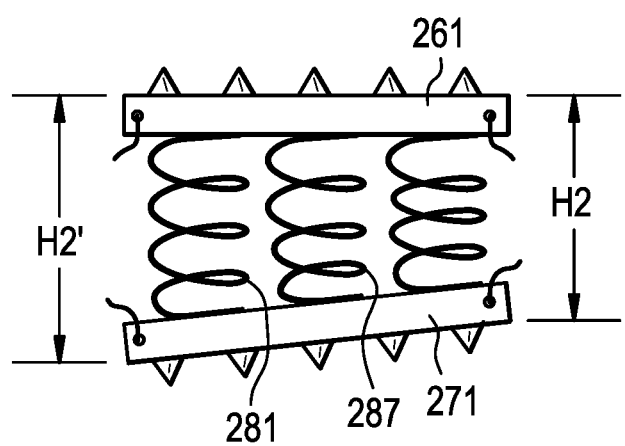

In accordance with FIGS. 19-20, there is provided an intervertebral device comprising;
a) A first endplate 261 having an outer surface 263 adapted for gripping a first natural endplate, an inner surface 265, an anterior end 267 and a posterior end 269,
b) a second endplate 271 having an outer surface 273 adapted for gripping a second opposed natural endplate, a lower surface 275, an anterior end 277 and a posterior end 279,
c) a first coil spring 281 having a first endportion 283 contacting the inner surface of the first endplate and a second endportion 285 contacting the inner surface of the second endplate,
d) a second coil spring 287 having a first endportion 289 contacting the inner surface of the first endplate and a second endportion 291 contacting the inner surface of the second endplate, wherein a first distance between the outer surfaces at the anterior ends of each endplate constitutes an anterior height, and wherein a second distance between the outer surfaces at the posterior ends of each endplate constitutes a posterior height, and the device having an unexpanded state and an expanded state, wherein each coil spring is tensioned in the unexpanded state and released in the expanded state, wherein the first and second coil spring provide varying tensions so that, in the released state, the anterior height is smaller than the posterior height.

Ellipse

Figure 21:
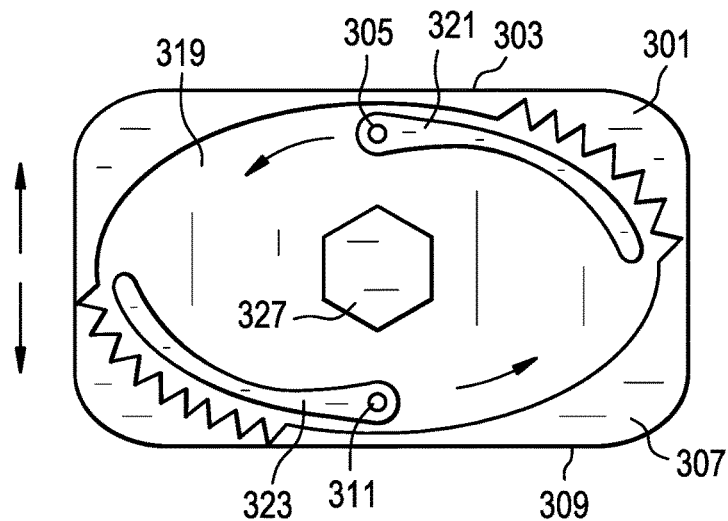
FIGS. 21-22 disclose an ellipse-based expandable design.
Figure 22:
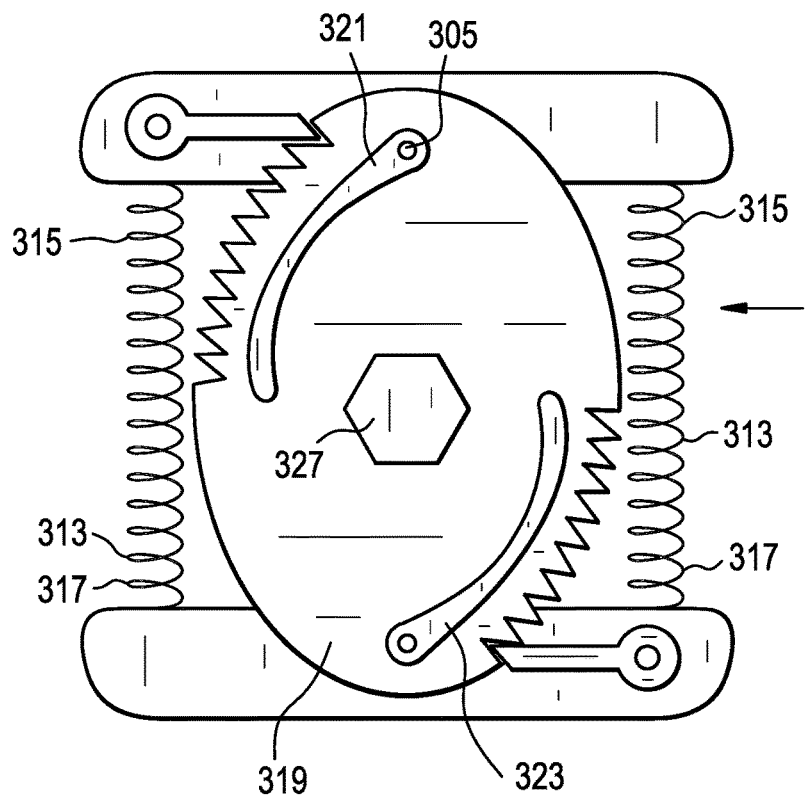

This FIGS. 21-22 embodiment has an elliptical body housed between two endplates. The ellipse has two opposed arcuate slots on its face that mate with a pair of pins placed substantially in the center of each endplate. A pair of springs are also provided between the two endplates on either side of the ellipse. These springs are compressed in the collapsed state of the implant. When the springs are release, they push the endplates apart and the ellipse rotates in accordance with the travel of the pins in the slots, thereby producing an expanded state for the implant.

In accordance with FIGS. 21-22, there is provided an intervertebral device comprising:
- a) an upper endplate 301 having an upper surface 303 and an upper pin 305 extending therefrom in a direction substantially parallel to the upper surface,
- b) a lower endplate 307 having a lower surface 309 and a lower pin 311 extending therefrom in a direction substantially parallel to the lower surface,
- c) first and second compression springs 313, each spring having an upper endportion 315 attached to the upper endplate and a lower endportion 317 attached to the lower endplate,
- d) a substantially elliptical body 319 disposed between the upper and lower endplates and between the first and second springs, the body having:
  - i) a first dimension defining a height, a second dimension perpendicular thereto defining a width, wherein the height is greater than the width, a center, and a perimeter,
  - ii) an upper arcuate slot 321 therethrough and a lower arcuate slot 323 therethrough, and
  - iii) an actuation element 327 for rotating the body,
- wherein the upper pin is slidingly received in the upper arcuate slot and the upper pin is slidingly received in the upper arcuate slot,
- wherein the device has a collapsed state and an expanded state,
- wherein, when the device is the collapsed state, the body extends between the endplates substantially in the second dimension and the springs are in compressed states, and
- wherein, when the device is the expanded state, the body extends between the endplates substantially in the first dimension and the springs are in expanded states.
  - Preferably, the actuation element is a projection disposed substantially in the center of the substantially elliptical body.
  - Preferably, the actuation element is a recess disposed substantially in the center of the substantially elliptical body.
  - Preferably, the actuation element has a hexagonal shape and is disposed substantially in the center of the substantially elliptical body.
  - Preferably, the upper endplate has an upper pawl 329 and the body has an upper ratchet 331 upon its perimeter, wherein the upper pawl is engaged with the upper ratchet. preferably, the lower endplate has a lower pawl 333 and the body has a lower ratchet 335 upon its perimeter, wherein the lower pawl is engaged with the lower ratchet,
  - Preferably, the upper and lower pins extend substantially in the same direction.
  - Preferably, the upper and lower pins each extend substantially in the same direction.
  - Preferably, each endplate has first 336 and second 337 ends and each pin is located approximately halfway between the first and second ends.

Squid

In this FIG. 23-25*d* embodiment, an inserter having upper and lower flexible blades is provided. A shaft with a pusher at its end is advanced between the blades. The pusher has an acicular cross-section so that its height is less than its width. Rotation of the pusher causes the larger width of the pusher to extend between the endplates thereby distracting the disc space. An indicator is built in to the inserter that measures the amount of distraction and thus the height.

In some embodiments, the shaft can be retracted and an implant loaded in front of the pusher. The shaft can then be advanced to act as an inserter.

In accordance with FIGS. 23-25*d*, there is provided an intervertebral implant inserter, comprising:
- a) a elongated central body 341 having a distal end 343, a proximal end, an outer surface, and a longitudinal throughbore 349 therethrough,
- b) upper 351 and lower 353 blades, each blade having a distal end portion 355 and a base portion 357, the base portion of each blade pivotally coupled to the elongated central body,
- c) a shaft 359 having a longitudinal axis, wherein the shaft is advanceable within the throughbore and rotatable about the longitudinal axis, the shaft having a distal end 361 forming a pusher 363 having an acicular transverse cross-section,
- d) upper 365 and lower 367 endplates respectively detachably connected to the distal end portion of a respective blade.

Preferably, each endplate has an upper surface 369, a lower surface 371, and a central throughhole 373 extending from the upper surface to the lower surface.

Preferably, the inserter further comprises:
- e) a height indicator 375 attached to the elongated central body.

Figure 23:
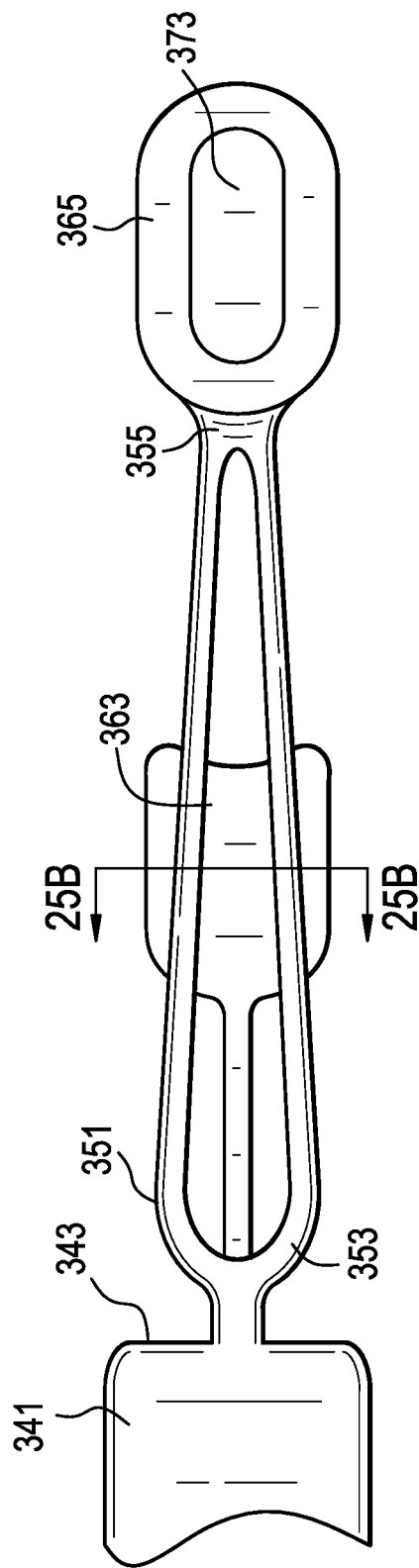
FIGS. 23-28 disclose an expandable device based upon floating blades.
Figure 24:
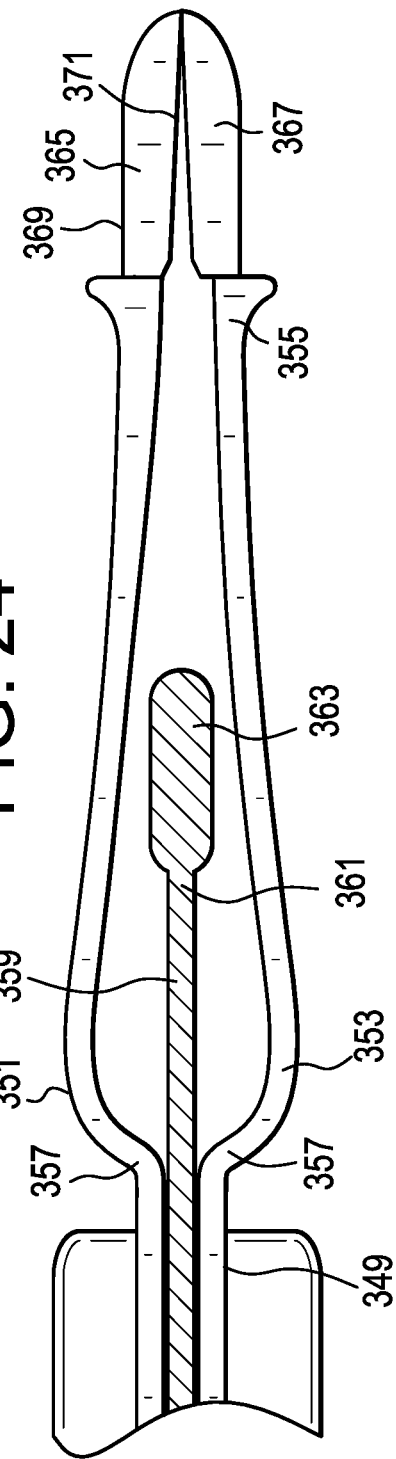
Figure 25A:
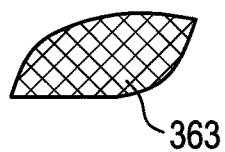
Figure 25B:
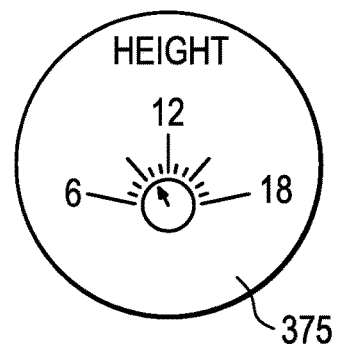
Figure 25C:
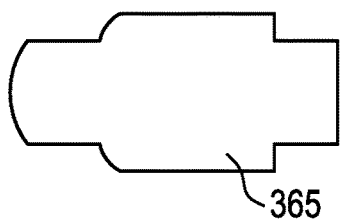
Figure 25D:
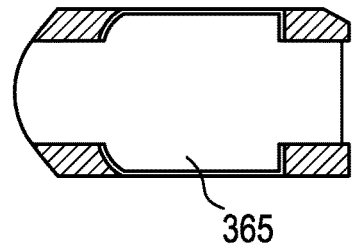

In some embodiments, there is an intervertebral assembly comprising:
- a) the inserter of FIG. 23, and
- b) a spacer disposed between the endplates and having an upper surface, a lower surface, and vertical throughhole extending between its upper and lower surfaces.

Preferably, the upper surface of the spacer is substantially uniplanar with the upper surface of the upper endplate, and the lower surface of the spacer is substantially uniplanar with the lower surface of the lower endplate.

Preferably, the vertical throughhole of the spacer substantially aligns with the central throughhole of each endplate.

In some embodiments, there is provided an intervertebral assembly comprising:
- a) the inserter of FIG. 23, and
- b) a spacer disposed distal of and in contact with the pusher, the spacer having an upper surface, a lower surface, and vertical throughhole extending between its upper and lower surfaces.

Reverse Squid

Figure 26:
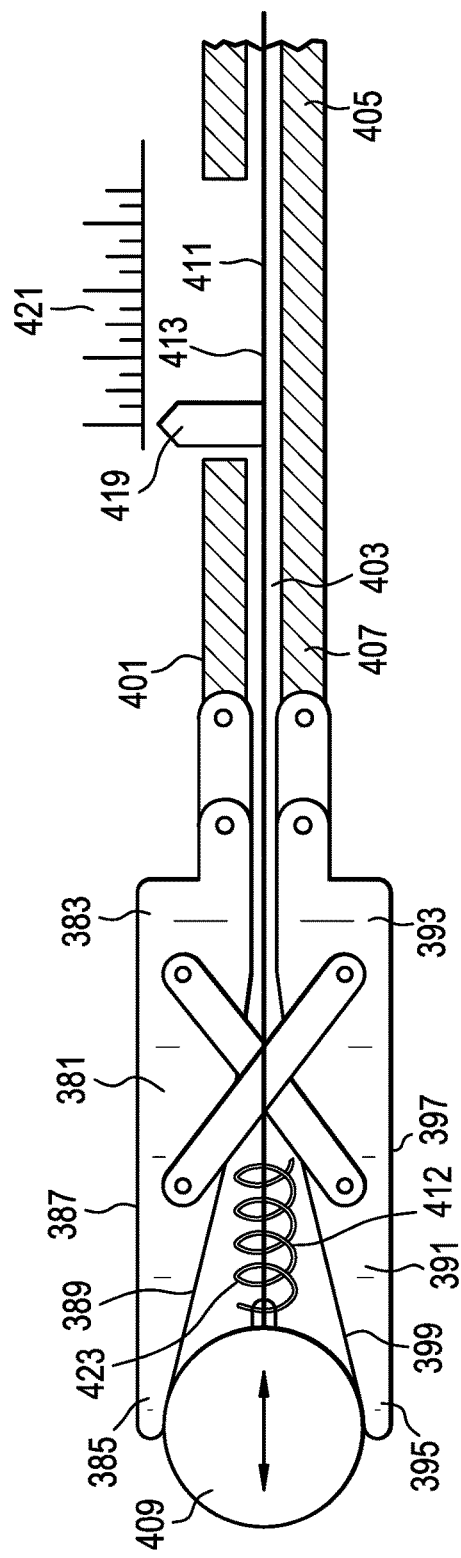
Figure 28:
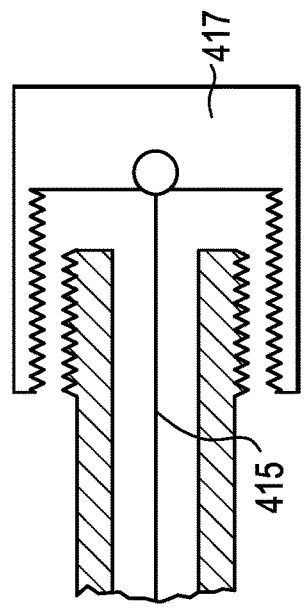
Figure 27:
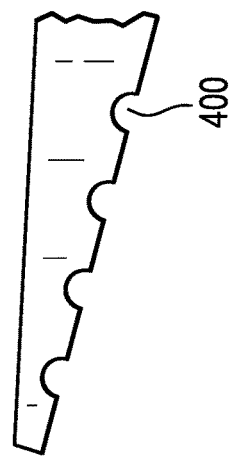

In the FIG. 26-28 embodiment, a core is provided between two ramped surfaces and caused to move between them, thereby increasing the distance between the two ramped surfaces. As the knob of the device is turned, the knob pulls the cable proximally, thereby pulling wedged core proximally as well. An indicator on the cable indicates the height achieved by the activity. In some embodiments, a second core is provided that indicates the angle of lordosis. In some embodiments, the ramped surfaces have indents or other such markings that provide height increments. In some embodiments, a spring is wrapped around the distal end portion of the cable, thereby allowing retraction of the core and bring the device back to its collapsed state.

In other embodiments, a wedged core is advanced forward instead of being retracted to allow for indications of height and lordotic angle.

In accordance with FIGS. 26-28, there is provided, an intervertebral trial, comprising;
- a) an upper endplate 381 having a proximal end portion 383, a distal end portion 385, an upper surface 387 and a lower surface 389 disposed at an acute angle from the upper surface,
- b) a lower endplate 391 having a proximal end portion 393, a distal end portion 395, a lower surface 397 and an upper surface 399 disposed at an acute angle from the lower surface,
- c) a tube 401 having a throughbore 403, a proximal end portion 405, and a distal end portion 407 pivotally attached to the proximal end of each endplate
- d) a spacer 409 disposed between a the distal end portions of the endplates and biased against the lower surface of the upper endplate and the upper surface of the lower endplate,
- e) a cable 411 having a distal end portion 412 attached to the spacer, an intermediate portion 413 disposed within the throughbore of the tube, and a proximal end portion 415,
- f) a knob 417 threadably attached to the proximal end portion of the tube and connected to the proximal end portion of the cable,
- g) an indicator 419 extending from the cable, and
- h) a first indicia of distance 421 attached to the tube and adapted to measure changes of position of the indicator.

wherein proximal movement of the cable causes the spacer to move proximally, thereby causing the upper surface of the upper endplate and lower surface of the lower endplate to move apart a distance that is conveyed by the viewing the indicator against the first indicia of distance.

Preferably, the trial further comprises:
- i) a spring 423 disposed about the distal end portion of the cable.

Preferably, at least one of the lower surface of the upper endplate and the upper surface of the lower endplate comprises a second indicia of distance.

Preferably, the upper surface of the upper endplate and the lower surface of the lower endplate are substantially parallel.

Now referring to FIG. 27, as the ball 409 is pulled back, the ball will rest in the indents 400 within the trail arms. The small indents are spaced apart for different trail heights. The ball position will indicate the heights on the disk space.

Gears

Figure 29:
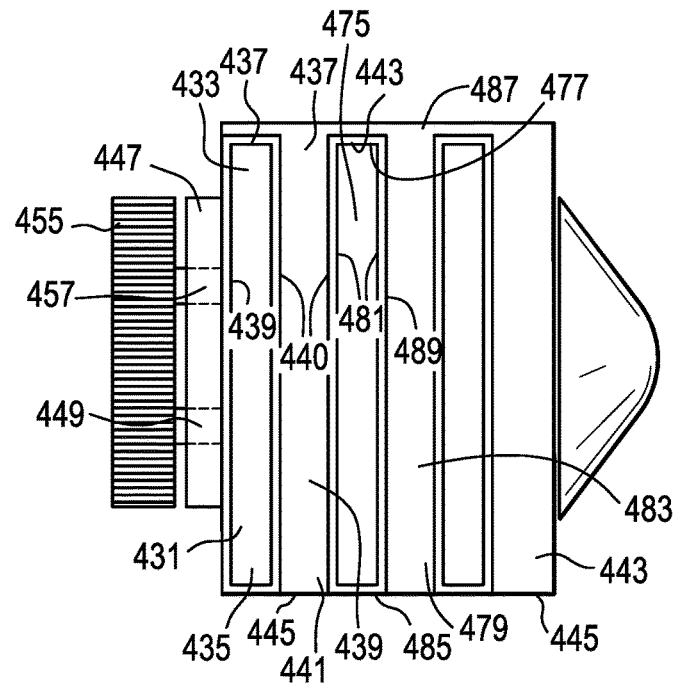
FIGS. 29-31 disclose an expandable device based upon gears.
Figure 30:
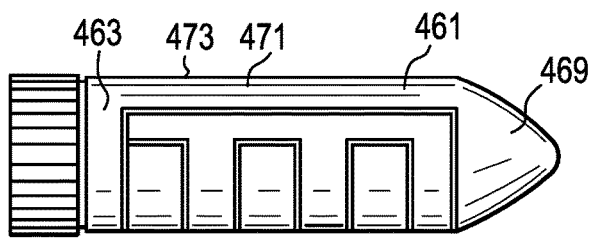
Figure 31:
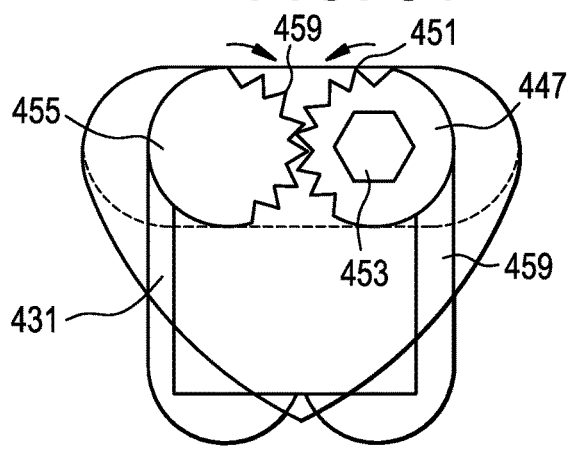
Figure 32:
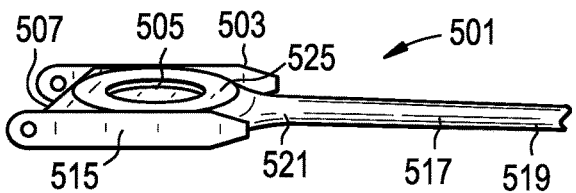
FIGS. 32-38 disclose an expandable design based upon a box chisel.
Figure 33:
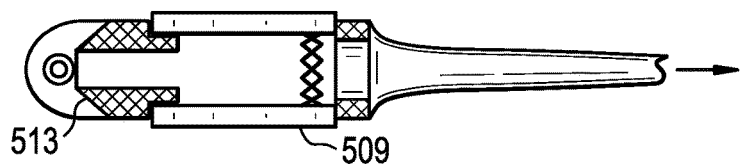
Figure 34:
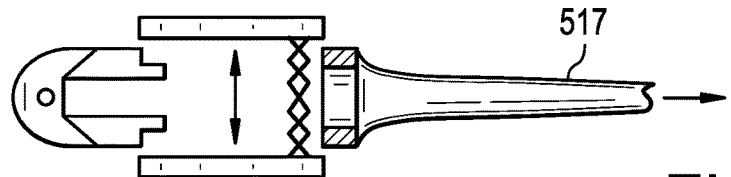
Figure 36:
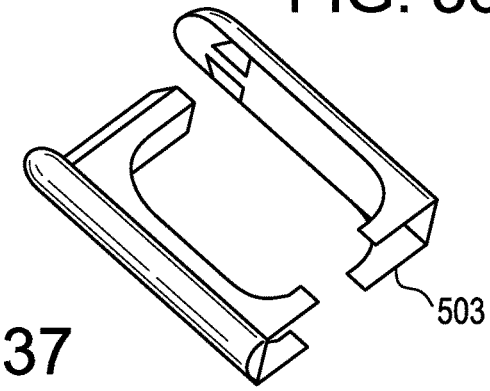
Figure 35:
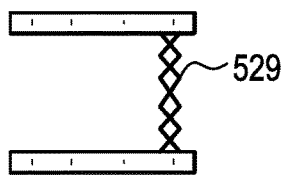
Figure 37:
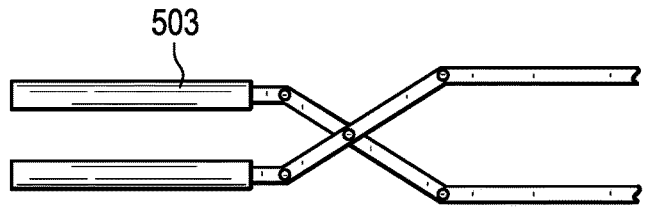
Figure 38:
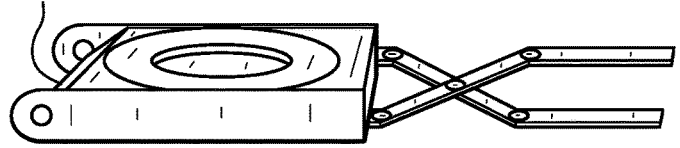

Now referring to FIGS. 29-31, there is provided an expandable intervertebral device in which two sets of parallel flanges are pivoted from a collapsed configuration in opposite directions about 90 degrees to produce an expanded configuration capable of distracting a disc space. In some embodiments, the sets of flanges are attached on opposite sides of a fixed carriage. The opposite pivoting of the flanges (i.e., clockwise and counterclockwise) is accomplished by rotating a pair of interlocked gears respectively connected to the first and second flanges. The rotation can be accomplished by inserting a driver into a driving connection on one of the gears and rotating the driver to cause opposed rotation of the gears and thereby opposed pivoting of the sets of flanges. The pivoting can be stopped and locked after the desired amount of distraction is achieved.

In some embodiments, the device is used as a trial to measure the amount of distraction, preferably as a prelude to inserting an expandable cage. The amount of distraction can be measured by measuring the amount of gear rotation. If the expandable cage has a lordotic feature, then the ratio of the gear diameters can be less than one to provide the required lordosis. Accordingly, the amount of angle produced can also be measured by measuring the extent of rotation in these different diameter gears.

In some embodiments, both gears can operate independently of each other by the use of a toggle switch in order to obtain precise angulation of the spacer.

In accordance with FIGS. 29-31, there is provided: an intervertebral device comprising:
- a) a first elongate flange 431 having a first end portion 433, a second end portion 435 and a pair of lateral sidewalls 437,
- b) a second elongate flange 439 having a first end portion 441, a second end portion 443 and a pair of lateral sidewalls 445,
- c) a first gear 447 connected to the first flange by a first pin 449, the first gear having a plurality of teeth 451 and a driving connection 453,
- d) a second gear 455 connected to the second flange by a second pin 457, the second gear having a plurality of teeth 459,
- e) a carriage 461 comprising a proximal wall 463 having first and second throughholes extending in the proximal-distal direction, a distal wall 469 and a bottom wall 471 connecting the proximal and distal walls, wherein the bottom wall has a bottom surface 473, wherein the teeth of the first and second gears are interlocked, wherein the first and second pins respectively pass through the first and second throughholes and respectively connect to the first end portions of the first and second flanges, wherein the device has a collapsed configuration in which the sidewalls of the elongate flanges are substantially parallel to the bottom surface, wherein rotation of the gears in the collapsed configuration produces in the device an expanded configuration in which the sidewalls of the elongate flanges are substantially perpendicular to the bottom surface.

Preferably, the device further comprises:
- f) a third elongate flange 475 having a first end portion 477, a second end portion 479 and a pair of lateral sidewalls 481,
- g) a fourth elongate flange 483 having a first end portion 485, a second end portion 487 and a pair of lateral sidewalls 489, wherein the first and second pins respectively pass through the first and second flanges and respectively connect to the first end portions of the third and fourth flanges, thereby respectively connecting the first and second pins to the third and fourth flanges, wherein the first and third elongate flanges are substantially parallel in the collapsed and expanded configurations, wherein the second and fourth elongate flanges are substantially parallel in the collapsed and expanded configurations, Preferably, each flange has a second end and wherein, in an expanded configuration, a distance between the bottom surface of the bottom wall of the carriage and the second end of each flange corresponds substantially to the height of a disc space.

Preferably, each flange comprises a narrowed intermediate section 493 between the first and second end portions.

Box Chisel

In the FIG. 32-38 embodiment, a four-sided osteotome is modified to house a pair of endplates connected by an expansion mechanism. In use, the osteotome is used as a box chisel to shape the disc space, and then the expansion mechanism is actuated to eject the endplates away from the rest of the osteotome, thereby providing a basis for an implant.

In accordance with FIGS. 32-38, there is providedan expandable intervertebral box chisel, comprising;
a) a four-sided osteotome 501 comprising i) an upper wall 503 having a vertical throughhole 505 and a sharpened distal edge 507 and ii) a lower wall 509 having a vertical throughhole and a sharpened distal edge 513, and iii) opposed sidewalls 515 connected the upper and lower walls,
b) a shaft 517 having a proximal end portion 519 and a distal end portion 521 connected to the osteotome,
c) a handle 523 connected to the proximal end portion of the shaft, and
d) upper 525 and lower endplates disposed in the respective vertical throughholes and connected by an expansion mechanism 529, wherein the chisel has a collapsed configuration in which the endplates are disposed in the throughholes and separated by a first distance and an expanded configuration in which the endplates are moved further apart and out of the throughholes, and are separated by a second distance greater than the first distance.

Preferably, the expansion mechanism comprises a spring.
Preferably, the expansion mechanism comprises a ratchet.
Preferably, the upper and lower walls are pivotally attached at a first pivot junction proximal to the osteotome.

We claim:

1. An intervertebral device, comprising:
a) a first strut comprising i) an upper portion forming an upper surface having teeth adapted for gripping an upper natural endplate and ii) a lower portion forming a lower surface comprising teeth adapted for gripping a lower natural endplate,
b) an upper arm pivotally connected to the upper portion of the first strut by an upper pivot pin and having an upper surface having teeth adapted for gripping the upper natural endplate,
c) a lower arm pivotally connected to the lower portion of the first strut and having a lower surface having teeth adapted for gripping the lower natural endplate, and
d) a second strut extending between a lower surface of the upper arm and an upper surface of the lower arm adapted for locking the device in an expanded condition,
wherein the upper surface of the first strut and the upper surface of the upper arm are substantially parallel in the expanded condition,
wherein the lower surface of the first strut and the lower surface of the lower arm are substantially parallel in the expanded condition,
wherein the upper pivot pin does not pass through the upper surface of the first strut, and
wherein the teeth of the first strut extend in a direction substantially perpendicular to the upper pivot pin.

2. The device of claim 1 wherein the pivotal connections between the first strut and each arm each form a ratchet connection adapted to lock the device in the expanded condition.

3. The device of claim 1 wherein each of the lower surface of the upper arm and the upper surface of the lower arm comprises a recess adapted for reception of a respective end of the second strut.

4. The device of claim 1 wherein each arm has a first endface opposite its pivotal connection, and the first endfaces are substantially opposed in an unexpanded condition.

5. A method of using an intervertebral device, comprising the steps of:
a) inserting the intervertebral device of claim 1 into a disc space in its unexpanded condition,
b) moving each arm so that the device adopts its expanded condition, and
c) locking the device in its expanded condition.

6. An intervertebral device, comprising:
a) a first strut comprising i) an upper portion forming an upper surface having teeth adapted for gripping an upper natural endplate and ii) a lower portion forming a lower surface comprising teeth adapted for gripping an lower natural endplate,
b) an upper arm pivotally connected to the upper portion of the first strut by an upper pivot pin and having an upper surface having teeth adapted for gripping the upper natural endplate,
c) a lower arm pivotally connected to the lower portion of the first strut and having a lower surface having teeth adapted for gripping the lower natural endplate, and
d) a second strut extending between a lower surface of the upper arm and an upper surface of the lower arm adapted for locking the device in an expanded condition,
wherein the upper surface of the first strut and the upper surface of the upper arm are substantially parallel in the expanded condition,
wherein the lower surface of the first strut and the lower surface of the lower arm are substantially parallel in the expanded condition,
wherein the upper pivot pin extends substantially parallel to the upper surface of the first strut, and
wherein the teeth of the first strut extend in a direction substantially perpendicular to the upper pivot pin.

* * * * *